Figure 1:
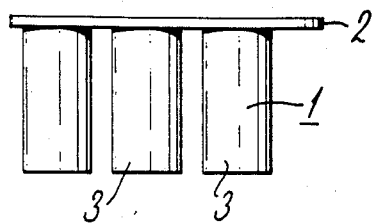

United States Patent [19]

Kukka et al.

[11] Patent Number: 4,684,250
[45] Date of Patent: Aug. 4, 1987

[54] SET OF CUVETTES

[75] Inventors: Aarre Kukka; Jukka Tervamäki; Heikki Nikulin, all of Helsinki; Olavi Vuorinen, Kerava, all of Finland

[73] Assignee: Labsystems Oy, Helsinki, Finland

[21] Appl. No.: 684,285

[22] Filed: Dec. 20, 1984

[30] Foreign Application Priority Data

Dec. 22, 1983 [FI] Finland .................. 834756

[51] Int. Cl.⁴ .......................................... G01N 21/03
[52] U.S. Cl. ...................................... 356/246; 356/440
[58] Field of Search ............................. 356/246, 440

[56] References Cited

U.S. PATENT DOCUMENTS 3,964,867 6/1976 Berry ............................... 356/246 X
4,431,307 2/1984 Suovaniemi ...................... 356/440 X Primary Examiner—Davis L. Willis
Assistant Examiner—Matthew W. Koren
Attorney, Agent, or Firm—Hopgood, Calimafde, Kalil, Blaustein & Judlowe

[57] ABSTRACT

A set of cuvettes wherein the measurement windows (5) are in the bottom of the cuvettes and surrounded by a matt-faced area (8). The matt-faced area eliminates the access of diffused light to the detector of the photometer.

5 Claims, 4 Drawing Figures

U.S. Patent        Aug. 4, 1987        4,684,250

SET OF CUVETTES

The present invention is concerned with a set of cuvettes for the reading of the results of virological, bacteriological and haematological reactions or for the spectrophotometric measurement of chemical colour reactions, wherein a beam of light is directed so as to pass through the liquid column to be measured and through the bottom of the cuvette defining the said column of liquid, in the direction of the longitudinal axis of the cuvette from a source of light placed at one side of the cuvette to a detector placed at the other side of the cuvette.

In prior art, similar sets of cuvette are known, e.g., as described in the Finnish Patent No. 57,665 (equivalent to the British Patent No. 1,486,210). They have, involved the drawback of the access of diffused light to the detector if the area of the bottom of the cuvette is considerably larger than the area of the beam of light passing through the bottom of the cuvette.

A test tray containing test wells with tiny transparent bottom windows is known from the U.S. Pat. No. 3,773,426. This tray, however, has to be made of two different materials which makes the process uncomfortable in practice.

The object of the invention has been to create a set of cuvettes in which the access of diffused light to the detector is eliminated, but which sets still can be made of one material.

Now a set of cuvettes has been invented in which the bottom of the cuvette is made of two parts so that in the middle of the bottom there is a polished area well penetrable by light and at the edges of the bottom there is a dim matt-faced annular area, from which any diffused light is scattered to the surroundings with only little of it reaching the detector.

The area is preferably annular, but any other form is also possible, e.g. such a form as makes the measurement window square.

It is an additional advantage of the set of cuvettes in accordance with the invention that in the so-called EIA-technique, by means of a so-called sensitizing procedure, more biological molecules can be made to adhere to the matt-faced area on the bottom of the cuvette than to the polished face. This results from the fact that the contact face with the plastic is larger on the matt face as compared with the polished area.

Figure 2:
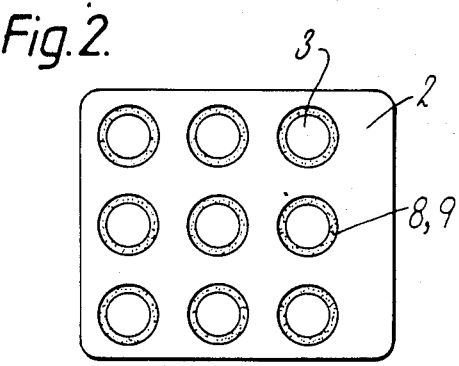
Figure 3:
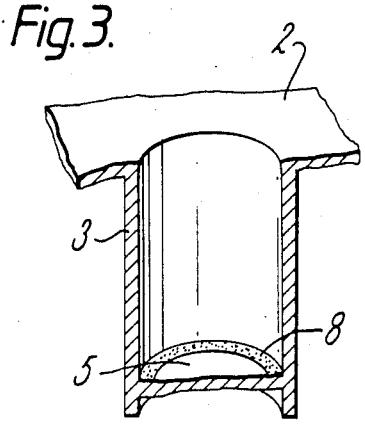
Figure 4:
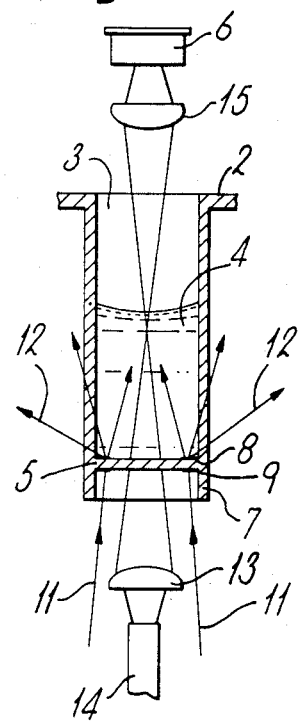

The invention comes out in more detail from the following description and from the attached drawings, wherein FIG. 1 is a side view of the set of cuvettes, FIG. 2 shows the set of cuvettes as viewed from above, FIG. 3 shows an individual cuvette as viewed three-dimensionally and in section, FIG. 4 shows an individual cuvette with the source of light and with the detector as viewed from the side and in section.

The support plate 2 of the set of cuvettes 1 is provided with several cuvettes 3 placed at certain distances from each other. These function as cuvettes when the absorbance of a solution 4 present in the cuvette 3 or the change in the intensity of light caused by a sediment on the bottom of the cuvette 3 or by turbidity is being measured by means of the principle of vertical measurement. The light passes from the source of light 14 through a lens 13 and through the bottom 5 of the cuvette 3, and the intensity of the light is recorded through a lens 15 by the detector 6 placed above the cuvette.

The measurement window 5 of the cuvettes 3 in the set of cuvettes 1 is surrounded from the outside by a cylindrical part or edge 7, which protects the measurement window from contamination and scratches, whereby the measurement windows 5 of the cuvettes in the set of cuvettes remain as of optically high standard. If the bottom 5 of the cuvettes 3 in the set of cuvettes 1 is plane, the bottom of the cuvette is easy to manufacture by conventional plastic techniques. No optical errors are produced, nor a lens effect on the passage of the light.

The edges of the measurement windows 5 of the cuvettes 3 are provided with annular, matt-faced areas 8 and 9 either on one side or on both sides of the windows. The beam of measurement light that passes through the bottom window 5 of a cuvette has preferably a diameter clearly smaller than that of the annular matt-faced area 8, whereby the matt face 8 does not affect the passage of the measurement light. On the contrary, any diffused light 11 arriving from the surroundings or reflected from the bottom is scattered 12 from the matt face 8 in all directions, whereby only a small fraction of the diffused light 11 ends up on the detector 6.

The area of the annular matt-faced part 8 on the bottom of the cuvette is larger than the area of the polished face. This can be taken advantage of in the so-called EIA-technique, wherein, by means of a so-called sensitizing procedure, biological molecules, such as antigens or antibodies, are made to adhere to the plastic walls of the cuvette. Since the contact face between the liquid and the plastic becomes larger within the matt-faced area, on sensitization, more molecules adhere to the plastic face than if the face had been made smooth by polishing. Thus, by means of the roughness of the matt-faced area, it is possible to control the properties of the cuvettes sensitized for the EIA-technique. Most advantageously, the roughness, i.e. the R-value, can be adjusted to the appropriate and desired level by means of so-called arc machining.

What is claimed is:

1. A set of cuvettes comprising at least one cuvette having a measurement window in the bottom thereof, wherein said measurement window is surrounded by a matt-faced area, wherein said matt-faced area is on the inner surface of the bottom of said cuvette.

2. The set of cuvettes as claimed in claim 1, wherein said matt-faced area is of annular shape.

3. The set of cuvettes as claimed in claim 2, wherein said annular shaped matt-faced area is on the inner surface of the bottom of said cuvette.

4. The set of cuvettes as claimed in claim 2, wherein said annular shaped matt-faced area is on both the inner and outer surfaces of the bottom of said cuvette.

5. The set of cuvettes as claimed in claim 1, wherein said matt-faced area is on both the inner and outer surfaces of the bottom of said cuvette.

* * * * *